United States Patent [19]
Kitagawara et al.

[11] Patent Number: 5,386,118
[45] Date of Patent: Jan. 31, 1995

[54] METHOD AND APPARATUS FOR DETERMINATION OF INTERSTITIAL OXYGEN CONCENTRATION IN SILICON SINGLE CRYSTAL

[75] Inventors: Yutaka Kitagawara; Hiroshi Kubota; Masaro Tamatsuka; Takao Takenaka, all of Gunma; Kazuhisa Takamizawa, Fukushima, all of Japan

[73] Assignee: Shin-Etsu Handotai Co., Ltd., Tokyo, Japan

[21] Appl. No.: 38,694

[22] Filed: Mar. 29, 1993

[30] Foreign Application Priority Data

May 11, 1992 [JP]  Japan .................................. 4-144879
May 19, 1992 [JP]  Japan .................................. 4-151407

[51] Int. Cl.$^6$ ............................................ G01N 21/35
[52] U.S. Cl. .................................. 250/338.1; 250/340
[58] Field of Search ................. 250/338.1, 339, 340, 250/341

[56] References Cited

U.S. PATENT DOCUMENTS 4,590,574  5/1986  Edmonds et al. .................... 250/339
4,862,000  8/1989  Kubuta et al. ...................... 250/341
5,066,599  11/1991 Kaneta et al. ....................... 250/339

FOREIGN PATENT DOCUMENTS 0410737  1/1991  European Pat. Off. .

OTHER PUBLICATIONS

B. Pajot, et al., "Quantitative Spectroscopy of Interstitial Oxygen in Silicon", Dec. 1985, pp. 3034–3037, *Journal of the Electrochemical Society*, vol. 132, No. 12.
F. Shimura, et al., "Heterogeneous distribution of interstitial oxygen in annealed Cxochralski-grown silicon crystals", pp. 867–870, *Applied Physics Letters*, vol. 38, No. 11, 1 Jun. 1981.
G. K. Agopian, et al., "Determination of Interstitial Oxygen in Silicon Using Internal Calibration with Two Phonon Peaks", IBM Technical Disclosure Bulletin, pp. 1389–1390, vol. 23, No. 4, Sep. 1980.
K. G. Barraclouch, et al., "Calibration of Infrared Absorption by Gamma Activation Analysis for Studies of Oxygen in Silicon", Journal of the Electrochemical Society, pp. 187–191, vol. 133, No. 1, Jan. 1986.
Disclosed anonymously, "Spectroscopic Determination of Wafer Thickness for Measurement of Interstitial Oxygen by Dispersive Infra-red Spectroscopy", Research Disclosure, p. 216, Havant GB, Apr. 1986.

*Primary Examiner*—Paul M. Dzierzynski
*Assistant Examiner*—Richard Hanig
*Attorney, Agent, or Firm*—Ronald R. Snider

[57] ABSTRACT

A method and apparatus disclosed by this invention allows determination of the interstitial oxygen concentration in a silicon single crystal to be effected stably and accurately without being appreciably affected by change of the temperature of a sample under test. The interstitial oxygen concentration in the silicon single crystal is determined on the basis of the value of:

(Light absorption coefficient)×[1+a×(peak half width)]

or the value of:

(Light absorption coefficient)×[1+b×(peak area)/(peak height)]

(wherein a or b stands for a parameter whose value depends on the conditions for determination or the apparatus for determination and should be empirically fixed with respect to specific conditions of determination or the apparatus used therefor) concerning an interstitial oxygen absorption peak at 1106 cm$^{-1}$ obtained by means of an infrared spectrophotometer.

5 Claims, 11 Drawing Sheets

METHOD AND APPARATUS FOR DETERMINATION OF INTERSTITIAL OXYGEN CONCENTRATION IN SILICON SINGLE CRYSTAL

BACKGROUND OF THE INVENTION

1. Field of the Invention

This invention relates to a method and apparatus for determining accurately an interstitial oxygen concentration in a silicon single crystal.

2. Description of the Prior Art

Heretofore, the Czochralski (CZ) method has been adopted for the operation of pulling a silicon single crystal. It has been known that this method requires use of a crucible made of quartz for accomodating a molten silicon mass and that this method, therefore, entails a possibility that the oxygen contained in the crucible of quartz will be melted out and passed into the molten silicon mass and eventually incorporated in the silicon single crystal. The oxygen which is thus incorporated into the silicon single crystal persists in the form of an interstitial oxygen in the silicon single crystal. Some oxygen atoms collect into clusters and persist in a precipitated state.

The oxygen which thus persists in the silicon single crystal at times forms a defect which induces an impairment of the characteristic properties of a transistor as a device using the silicon single crystal and at other times produces an useful effect as in manifesting a gettering effect or enhancing mechanical strength of a wafer in the production of an integrated circuit. Thus, the desirability of developing a technique for accurately determining the interstitial oxygen concentration ("Oi") in a silicon single crystal has been finding growing recognition. Particularly for the purpose of coping with the high degree of integration prevailing recently, the "Oi" in the single crystal Si substrate to be used must be controlled accurately on the order of 0.1 ppma or the order of 0.01 ppma. Thus, a need is felt strongly for a method and apparatus which determines the "Oi" with high accuracy enough to suit the evaluation aimed at.

Heretofore, for the determination of the interstitial oxygen concentration [Oi] in a silicon single crystal, the method which relies on the absorption of the interstitial oxygen in the infrared local vibration mode, namely the method which effects the determination of the interstitial oxygen concentration by finding the light absorption coefficient $\alpha_o$ of the interstitial oxygen [Oi] with respect to the absorption peak at 1106 cm$^{-1}$ at normal room temperature and multiplying the light absorption coefficient $\alpha_o$ by the concentration conversion coefficient k as shown below.

$$[Oi] = k\alpha_0 \qquad \text{[Formula 1.]}$$

has been known as the most fundamental of all the methods known in the art.

In accordance with a report by Japan Electronic Industry Development Association (JEIDA) [T. Iizuka et al., J. Electrochem. Soc., 132, 1707(1985)], the concentration conversion coefficient k is $3.03 \times 10^{17}$ cm$^{-2}$. The light absorption coefficient $\alpha_o$ is the physical quantity which is substantially proportional to the peak height of Oi absorption at 1106 cm$^{-1}$ as reported by T. Iizuka et al.. More specifically, it is the physical quantity which is found by correcting the slight deviation from the relation of proportions caused by the effect of multiple reflection within a given sample in accordance with the following formulas 2 and 3 using such parameters as the peak height and the sample thickness. In other words, the coefficient $\alpha_o$ can be determined by the method (JEIDA method) reported in the literature mentioned above.

For the determination of [Oi] of a Si crystal, the net infrared light transmittance T of the Oi local vibration is expressed under the existence of internal multiple reflection effect by the formula 2:

$$T = f(R, d, \alpha_1, \alpha_o)e^{-\alpha_o d} \qquad \text{[Formula 2]}$$

In the formula shown above, $f(R, d, \alpha_1, \alpha_o)$ is expressed by the following formula 3.

$$f(R, d, \alpha_1, \alpha_0) = \frac{1 - R^2 e^{-2\alpha_1 d}}{1 - R^2 e^{-2(\alpha_1 + \alpha_0)d}} \qquad \text{[formula 3]}$$

In the formula 3 shown above, R stands for the reflectance on the surface of the Si crystal which is R=0.30, d for the thickness of the oxygen-containing sample crystal and the reference crystal having an oxygen concentration below the lower limit of detection, $\alpha_1$ for the light absorption coefficient based on the vibration of the Si crystal lattice which is $\alpha_1=0.85$ cm$^{-1}$, and $\alpha_o$ or the light absorption coefficient based on the local vibration of interstitial oxygen atoms.

The determination of the net transmittance T is carried out as follows. First, the spectrum of the value $T_{sample}/T_{reference}$ which is obtained by dividing the transmittance $T_{sample}$ of the oxygen-containing sample crystal by the transmittance $T_{reference}$ of the reference crystal, namely the comparative spectrum. FIG. 4 shows the comparative spectrum in the Oi absorption wavelength range. In the diagram, the ratio $T_{peak}/T_{base}$ i.e. the ratio of the peak value $T_{peak}$ to the base value $T_{base}$ in the Oi absorption forms the net transmittance T in the Oi local vibration (in other words, $T=T_{peak}/T_{base}$).

In addition to the JEIDA method otherwise called A method described above, the method to be described herein below (B method) has been widely used in the industry for the determination of [Oi]. The formula 2 described above differs exclusively by the factor portion of the function for correction of multiple reflection, $f(R,d,\alpha_1\alpha_o)$, from the following Lambert-Beer's law which holds good on the assumption that no multiple reflection occurs within a given sample.

$$T = e^{-\alpha d} \qquad \text{[Formula 4]}$$

The B method presumes that the following formula 5 of approximation to which the Lambert-Beer's law applies with necessary modifications holds good.

$$T \approx e^{-\alpha_{o,eff} d_{eff}} \qquad \text{[Formula 5]}$$

In the formula $d_{eff}$ stands for the effective thickness of the sample. The reason for using the effective thickness $d_{eff}$ in the place of the actual sample thickness d in the formula 5 of approximation is that the effective length of light path is increased owing to the multiple reflection of the infrared light within the crystal as illustrated by way of a model in FIG. 5 and the effective thickness $d_{eff}$ consequently becomes somewhat larger than the actual thickness d.

This effective thickness $d_{eff}$ can be empirically fixed as a physical quantity which is proportionate to the peak height (p) of the LO+LA phonon at 738 cm$^{-1}$ in the absorbance spectrum ($A_{sample}$=log [1/$T_{sample}$]) of the sample crystal illustrated in FIG. 6, for example. In other words, the following expression is presumed.

$$d_{eff} \text{ (Constant)} \times \text{(Peak height p of } LO+LA \text{ phonon)} \quad \text{[Formula 6]}$$

By substituting the $d_{eff}$ found as described above and the net transmittance T due to the Oi vibration in the formula 5, the following formula 7 is derived regarding the effective absorption coefficient of Oi is fixed by the following formula 7.

$$\alpha_{o,eff} \approx \frac{1}{d_{eff}} \cdot \ln(1/T) \quad \text{[Formula 7]}$$

The interstitial oxygen concentration [Oi] is evaluated in accordance with the following formula 8, using the effective concentration conversion coefficient $k_{eff}$ which is fixed by the $\alpha_{o/eff}$ and the physical quantity of concentration found by measurment.

$$[Oi] \approx k_{eff} \alpha_{o,eff} \quad \text{[Formula 8]}$$

Since this method of determination utilizes the effective thickness $d_{eff}$ to be found by the method of infrared absorption as shown in the formula 6 and therefore obviates the necessity for measuring the actual sample thickness d, it is widely used in the industry on account of the advantage that it allows automatic measurement which renders unnecessary the measurement of thickness. This method, however, permits no exact evaluation of [Oi] because the formula 5 presumed by the method is only an approximation of the formula 2 for compensation of multiple reflection.

SUMMARY OF THE INVENTION

When the interstitial oxygen concentration in a silicon single crystal is determined by the method described above, this measurement entials the phenomenon that the temperature of the sample crystal is suffered to change in the process of measurement. This is because the atmosphere of the housing for the light source for the infrared spectrophotometer, the interferometer, the electric circuits, etc. is warmed even to a temperature failing in the range of 30° to 40° C. by the heat generated by the infrared light source and the electric circuits and the atmospheric gas of the housing flows through the opening into the sample chamber and, as a result, the interior of the sample chamber is warmed to a level of about 30° C. The internal temperature of the measuring chamber in which the sample crystal is normally stored is about 22° to 25° C. The sample crystal which is installed within the sample chamber of the infrared spectrophotometer, therefore, is warmed by the atmosphere of the sample chamber which has a higher temperature and the temperature of the sample crystal is gradually elevated thence with the elapse of time.

Even the evaluation of [Oi] by the formula 1 according to the JEIDA method (A method) or even the evaluation of [Oi] by the formula 8 according to the B method has no consideration for the effect to be produced by the elevation of the temperature of the crystal inside the sample chamber, namely the dependency of the outcome of the evaluation on the temperature of the sample. The values of evaluation of [Oi] in one and the same sample crystal found by the A method and the B method were plotted as the function of sample temperature. The results are shown by the marks ◇ and the marks ☐ in FIG. 3. The data indicate that both the A method and the B method have the problem that the values of evaluation of [Oi] decrease in accordance as the sample temperature increases. Particularly, the B method betrays conspicuous dependence on temperature and does not fit accurate determination of [Oi].

This invention (first through fourth aspects of the invention) is aimed at solving the problems which are incurred by the conventional method of determination as described above. The object (the first object) of this invention is to provide a method and apparatus for the determination of an interstitial oxygen concentration in a silicon single crystal, which eliminates the cause for disturbance in the determination of an interstitial oxygen concentrationin the silicon single crystal and enables the determination of the interstitial oxygen concentration to be effected stably and accurately.

In the case of an oxygen in a supersaturated state in a CZ-Si crystal, however other disadvantage remains which can not be solved by the above invention.

With respect to a CZ crystal as-grown or containing no oxygen precipitate, the practice of drawing a base line between 1300 cm$^{-1}$ and 900 cm$^{-1}$ by JEIDA method described above, or the practice of drawing the base line between in a narrow range of wave numbers as between 1150 cm$^{-1}$ and 1050 cm$^{-1}$ as described afterward herein with reference to FIG. 10 and so on (B method) is used, as means for establishing a spectrum base line to measure a peak length.

The values of evalation of [Oi] to be obtained produce no significant difference, no matter whether the A method or B method may be used.

In the case of an oxygen-precipitated crystal which is produced when the oxygen in a CZ-Si crystal in the supersaturated state forms an intracrystalline precipitate during the process of heat treatment, the infrared absorption spectrum of this crystal shows not only the absorption peak in the local vibration mode of the interstitial oxygen dissolved within the crystal but also the infrared absorption band due to the oxygen precipitated. Generally for the evaluation of [Oi], the antisymmetric streching mode of vibration at 1106 cm$^{-1}$ which shows the strongest absorption in all the interstitial oxygen absorption peaks is used. In the oxygen-precipitated crystal, the absorption band due to the oxygen precitate appears in the neighborhood of 1300 to 1000 cm$^{-1}$ superimposed on the absorption peak mentioned above.

FIG. 10 depicts this situation with the aid of a spectrum actually obtained of an oxygen-precipitated crystal (2 mm in thickness) having a oxygen precipitate concentration ($\Delta$[Oi]) of 7 ppma which was produced by subjecting an as-grown crystal having an initial oxygen concentration of 19 ppma (by the [Oi] scale adopted as the JEIDA standard) to a two-stage heat treatment (4 hours at 800° C. and 17 hours at 1000° C.). This oxygen-precipitated crystal shows a broad doublet oxygen precipitate absorption band having peaks at 1120 cm$^{-1}$ and 1220 cm$^{-1}$. Particularly, the absorption band at 1120 cm$^{-1}$ peak strongly overlaps the interstitial oxygen [Oi] absorption peak at 1106 cm$^{-1}$. It is, therefore, difficult to obtain the amount of the absorption due to Oi exclusively as distinctly separated from the absorption due to the oxygen precipitate. Moreover, since the spectral shape of the absorption band due to the oxygen precipitate is largely varied by the temperature and time of the heat treatment for the oxygen precipitation as reported by K. Tempelhoff and F. Spiegelberg in "Semiconductor Silicon 1977" (H. R. Huff and E. Sirtl, eds.), pp. 585-595, Electrochem. Soc., Princeton, N.J., 1977, exact separation of the Oi absorption at 1106 cm$^{-1}$ and the absorption due to the preciptated oxygen cannot be obtained by the determination at normal room temperature.

In FIG. 10, the amount of absorption corresponding to the actual interstitial oxygen Oi must be in the length of a-b indicated in the diagram. When the base line contemplated by the well-known A method is adopted, the length of a-d is regarded as representing the amount of Oi absorption. Thus, the A method is suffered to evaluate [Oi] higher (by the length of b-d) than the actual level. The base line contemplated by the B method is improved as compared with the base line contemplated by the A method. Since it nevertheless regards the length of a-c as representing the amount of Oi absorption, the B method is fated to evaluate [Oi] higher by the length of b-c than the actual value.

It is clearly noted from the description given thus far that in the determination of [Oi] in the oxygen-precipitated crystal, the peak height is obtained only in the form inclusive of the absorption band due to the oxygen precipitate, no matter whether the A method or the B method may be used. Thus, no exact determination can be attained. When the confidence value of [Oi] obtained by the low-temperature infrared absorption method which will be described specifically hereinbelow and the values of evaluation of [Oi] obtained by the A method and B method described above are compared, it is seen that the values of evaluation of [Oi] of the two methods deviate from the confidence value of [Oi] toward the higher side as shown in FIG. 11.

For the purpose of obtaining the reliable value of [Oi] without being affected by the precipitation of oxygen, it suffices to perform infrared absorption determination of the interstitial oxygen peak at 1130 cm$^{-1}$ at such a low temperature as 3.8 K. and separate the broad band of the absorption of oxygen precipitate and the sharp peak of the interstitial oxygen absorption. The infrared absorption spectrum which is obtained by this method is illustrated in FIG. 12. The hatched portion shown in the lower part of the diagram represents part of the broad absorption band due to the oxygen precipitation which is displayed as enlarged in a narrow range of wave numbers between 1180 and 1080 cm$^{-1}$. Since the sharp absorption peak due to the interstitial oxygen [Oi] appears at the position of 1136 cm$^{-1}$ in the absorption band which is broad and involves only a small change, the Oi absorption and the absorption of the oxygen precipitate can be distinctly separated by the base line of the Oi peak as indicated by the broken line in the diagram. The light absorption coefficient of Oi (exclusive of the portion of absorption due to the oxygen precipitate) which is obtained by the determination at the low temperature of 3.8 K. as described above can be converted into the value of the interstitial oxygen concentration by means of the concentration calibration curve for 3.8-k determination which has been obtained by the use of a separately prepared Si single crystal sample of standard oxygen concentration. Since this value of the interstitial oxygen concentration excludes the portion of absorption due to the oxygen precipitate, it constitutes itself the most reliable value of [Oi] in the oxygen-precipitated crystal. The reliable value of [Oi] shown along the horizontal axis of the diagram of FIG. 11 is the value of [Oi] obtained as described above.

The low-temperature infrared absorption method described above allows the reliable value of [Oi] to be obtained without being affected by the precipitation of oxygen in the crystal under test. On account of the very low temperature to be used for the determination, however, this method entails the disadvantage that the assumption by the sample of the state of low temperature is difficult, the procedure of determination is highly complicated, the desire to perform quickly the determination on a large number of samples is not easily fulfilled, and the determination requires use of an expensive apparatus.

This invention (the fifth aspect of the invention) is aimed at solving the above problems. The object (the second object) of this invention is to provide a method for the determination of an interstitial oxygen precipitate therein, which enables the interstitial oxygen concentration to be determined accurately at normal room temperature by a simple procedure without being obstructed by the oxygen precipitate.

BRIEF DESCRIPTION OF THE DRAWINGS

This invention will be better understood and the objects and features other than those set forth above will become apparent when consideration is given to the following detailed description thereof, which makes reference to the annexed drawings wherein.

DETAILED DESCRIPTION OF THE PREFERRED EMBODIMENTS

Figure 1:
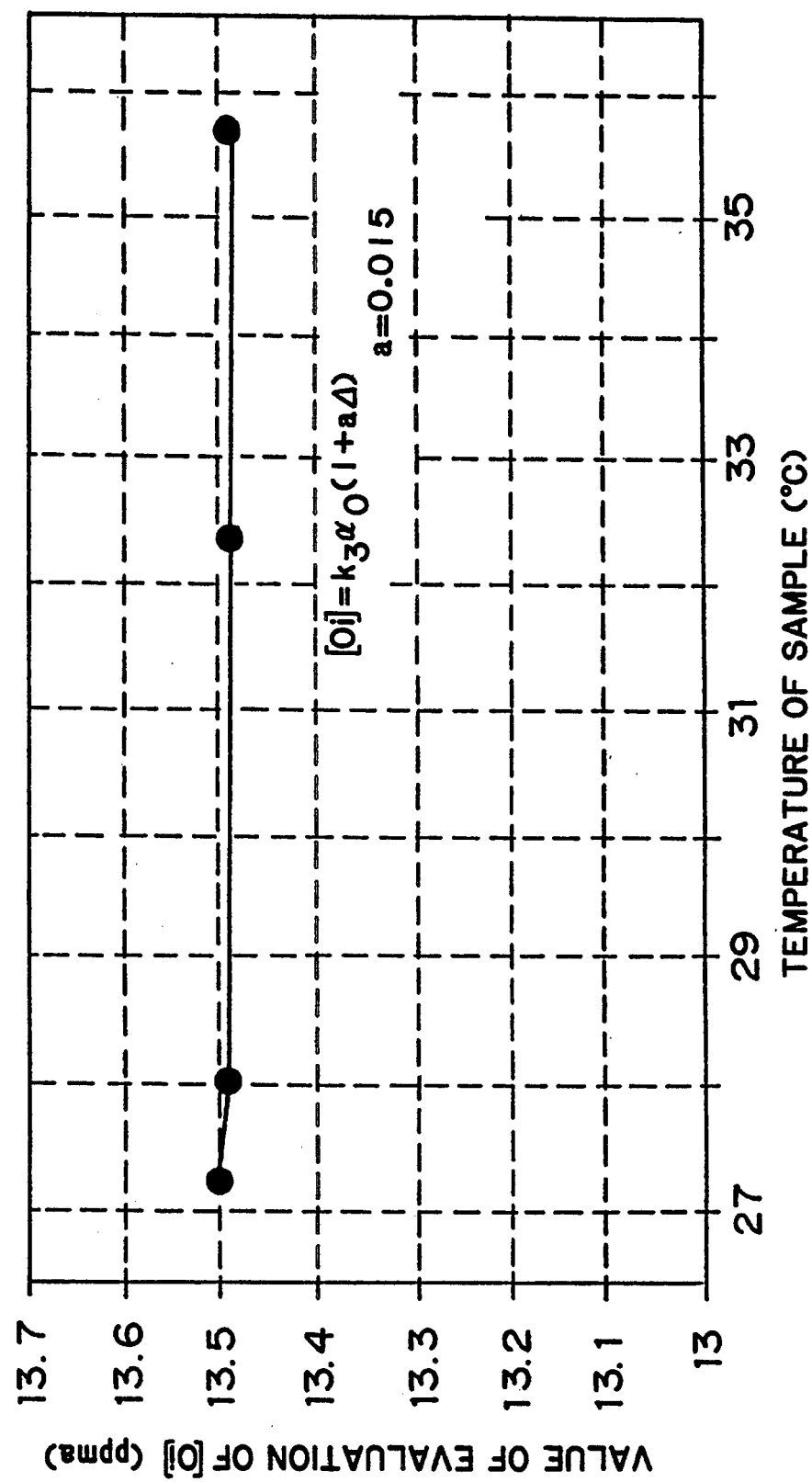
FIG. 1 is a graph showing the relation between the value of evaluation of oxygen concentration obtained by the method of determination according to the first aspect of this invention and the sample temperature.

The first aspect of this invention for accomplishing the first object mentioned above resides in a method for the determination of an interstitial oxygen concentration in a silicon single crystal by means of the absorption of the interstitial oxygen in the infrared local vibration mode, which method is characterized by effecting the determination of the interstitial oxygen concentration in the silicon single crystal by obtaining an absorption peak of the interstitial oxygen from the following value:

(Light absorption coefficient)$\times[1+a\times$ (peak half width)]

or the following value:

(Light absorption coefficient)$\times[1+b\times$ (peak area)/(peak height)]

(wherein the value of a or b is a parameter which depends on the conditions of determination or the apparatus for determination and which is empirically fixed with respect to the specific conditions of determination or the apparatus) concerning the absorption peak.

The second aspect of this invention resides in an apparatus for determination which is characterized by having temperature adjusting means disposed on a sample stage in a sample chamber of an infrared spectrophotometer.

The third aspect of this invention resides in an infrared spectrophotometer as an apparatus for determination comprising a light source for the infrared radiation, an incidence orifice for limiting the light from the light source and, at the same time, intercepting the part of the light impinging on an interferometer which is the angular range greater than an angle fixed by the diameter of the orifice of the optimum incidence, an interferometer provided with a translucent mirror, a stationary mirror, and a movable mirror, a sample chamber provided with a sample stage for fixation of a sample thereto and adapted to receive the light emitted from the interferometer, and a detector for detecting the light having entered in a sample and subsequently passed therethrough or reflected thereby after absorption of the part of light of the characteristic wave number peculiar to the sample, which apparatus is characterized by the fact that the space accommodating the light source and the interferometer and the space enclosing the sample chamber are partitioned from each other with a partition panel and other members of the sample chamber and the part for passing the infrared radiation is also partitioned perfected with an optical window member and the value of [Oi] is calculated in accordance with the method of determination described above and displayed.

The fourth aspect of this invention resides in an apparatus for determination which comprises a mechanism for inserting a sample under test into and removing the sample from a sample chamber by means of an automatic conveying device and a contacting or noncontacting mechanism for effecting automatic measurement of the thickness of the sample before or after the measurement of infrared absorption, performs comprehensive computerized control of the operations of determination of infrared absorption, measurement of sample thickness, computation of interstitial oxygen concentration, and conveyance of sample, and effects the determination of the interstitial oxygen concentration in the form of an automatic operation.

The fifth aspect of this invention for accomplishing the second object of this invention described above resides in amethod for determining an interstitial oxygen concentration in a silicon single crystal having oxygen precipitate therein by means of infrared absorption, which method is characterized by calculating the interstitial oxygen concentration of the silicon single crystal from the value of peak height, area, or (half width)$\times$(peak height) of the absorption peak based on the combination of the phonon linkage TA+TO of the silicon lattice appearing at 1720 cm$^{-1}$ at normal room temperature and the antisymmetric streching mode of vibration of Si$_2$O [B. Pajot et al., J. Electrochem. Soc., 132, 3034 (1985)].

The infrared absorption with the moisture in the air overlaps the absorption peak of Oi at 1720 cm$^{-1}$. The determination of the interstitial oxygen concentration in the silicon single crystal by means of this absorption peak, therefore, is characterized by having the interior of the housing of the spectrophotometer and the interior of the sample chamber thereof purged with an atmospheric gas incapable of showing any absorption near 1720 cm$^{-1}$ so as to prevent the absorption with the moisture from manifesting itself in the absorption peak.

Figure 10:
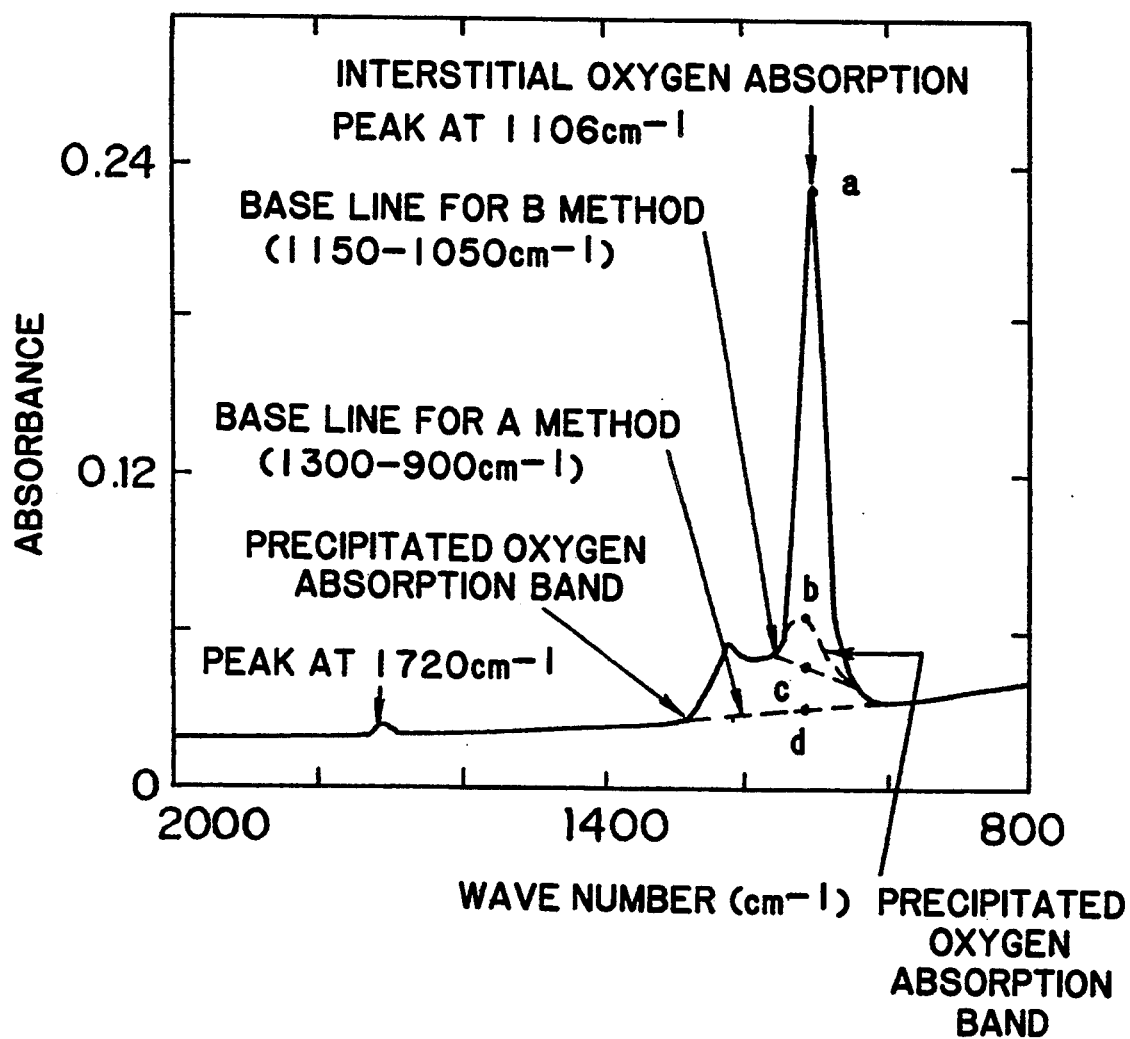
FIG. 10 is a graph showing the infrared absorption spectrum obtained of an oxygen-precipitated silicon single crystal by the FT-IR at normal room temperature and the base lines used by the A method and the B method.

The peak height of Oi at 1720 cm$^{-1}$ obtained at normal room temperature is so small as to account for 1/59 of the peak height at 1106 cm$^{-1}$ as shown in FIG. 10. It has been found that a highly sensitive Fourier-transform infrared spectrophotometer (FT-IR) is capable of determining with full accuracy the value of the peak height, area, or (half width)$\times$(peak height) of the absorption peak. This invention has been acomplished on the basis of this fact.

The method of this invention is also usable effectively for the determination of an interstitial oxygen concentration in a silicon single crystal having antimony incorporated therein in a high concentration.

The first through fourth aspects of this invention will be described more specifically below.

When the aforementioned A method (T. Iizuka et al.) or B method described previously is used for the determination of [Oi], the dependency of this determination on the sample temperature illustrated in FIG. 3 manifests clearly itself. This statement implies that in the determination by the A method, the light absorption coefficient $a_o$ in the formula 1 for conversion, [Oi]=-$ka_o$ (k for a constant), has dependency on the sample temperature. Since FIG. 3 covers the data of one and the same sample, the fact just mentioned means that the peak height of the Oi absorption peak at 1106 cm$^{-1}$ decreases in proportion as the temperature increases.

Figure 3:
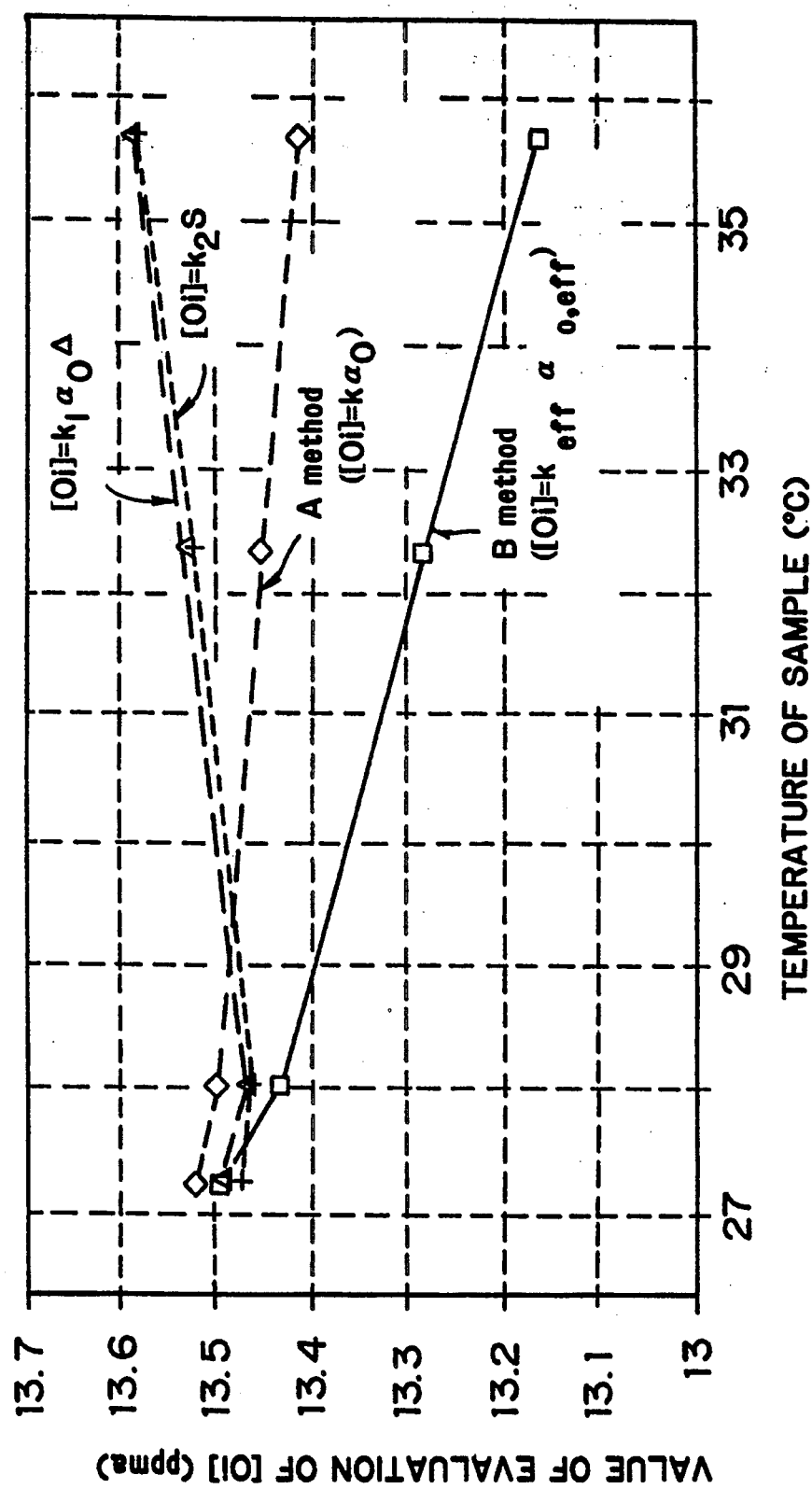
FIG. 3 is a graph showing the relation between the value of evaluation of the interstitial oxygen concentration obtained in Comparative Experiment 1 and the values of evaluation of oxygen concentration obtained by the formula 9 and the formula 10 on one part and the sample temperature on the other part.
Figure 4:
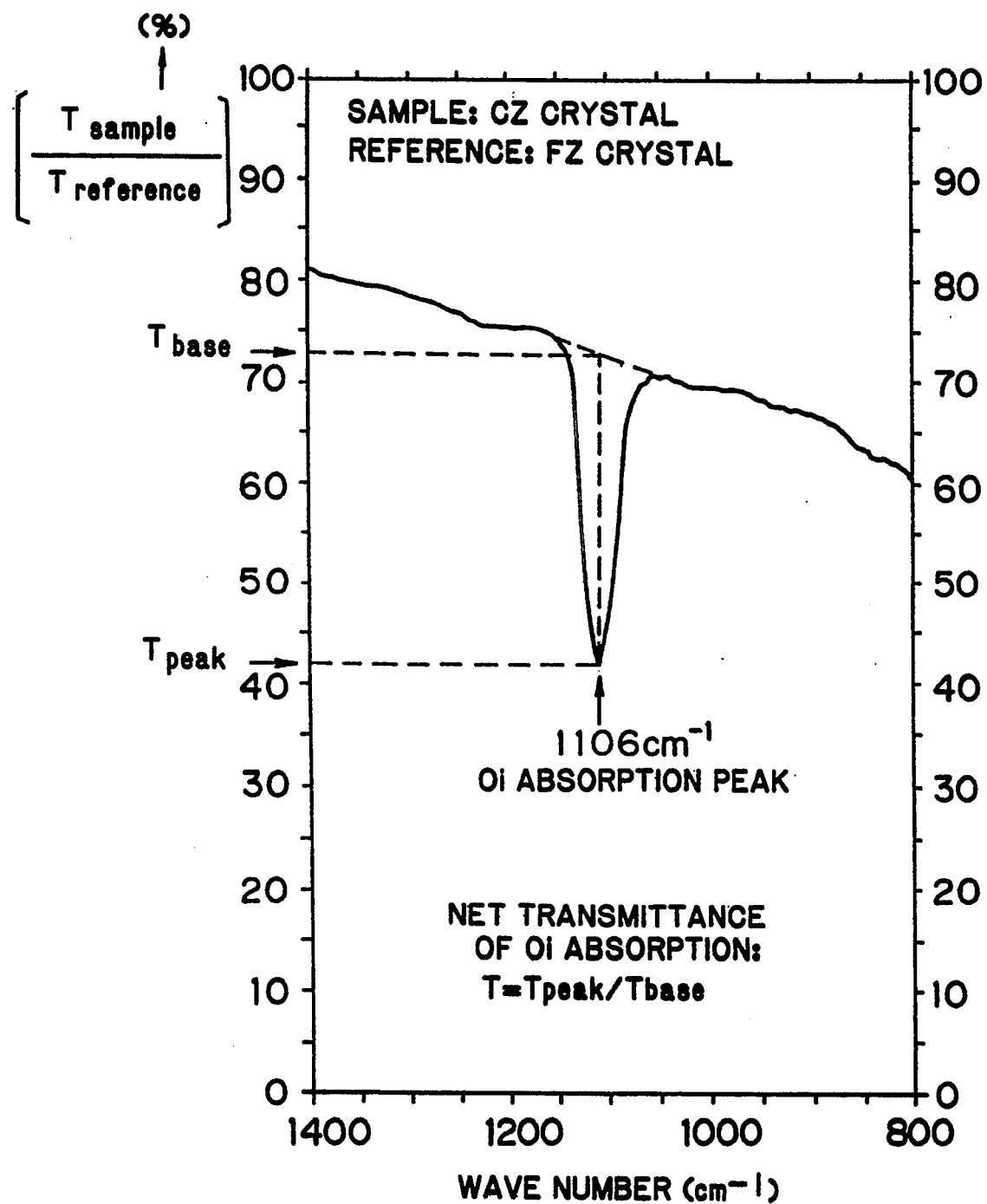
FIG. 4 is an explanatory diagram for defining the net transmittance of the infrared radiation through the interstitial oxygen.
Figure 5:
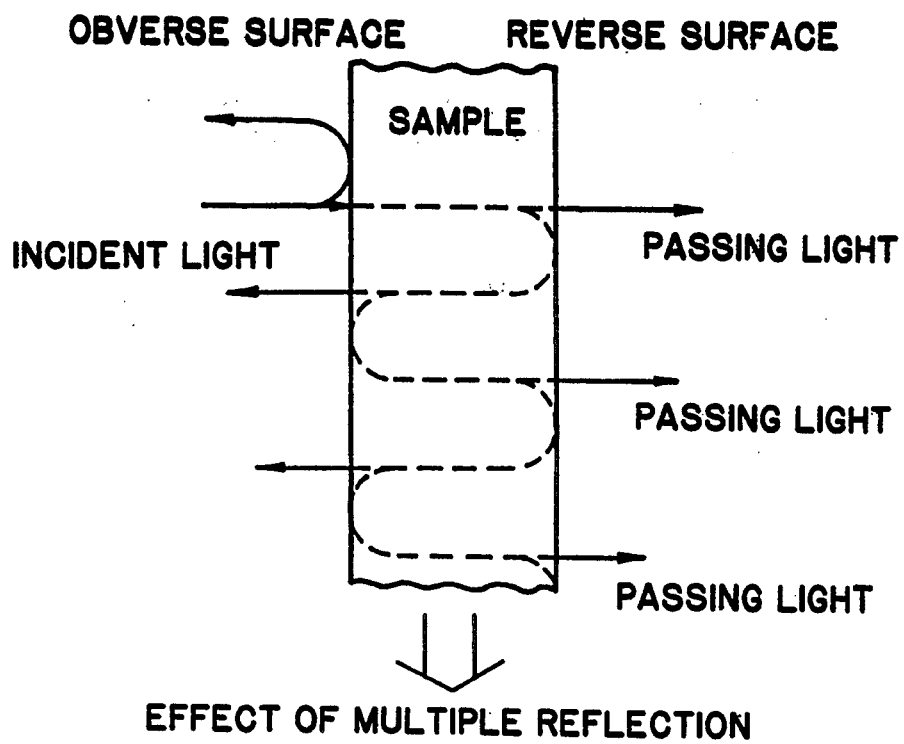
FIG. 5 is a model diagram for aiding in the explanation of the effect of multiple reflection within the sample.
Figure 6:
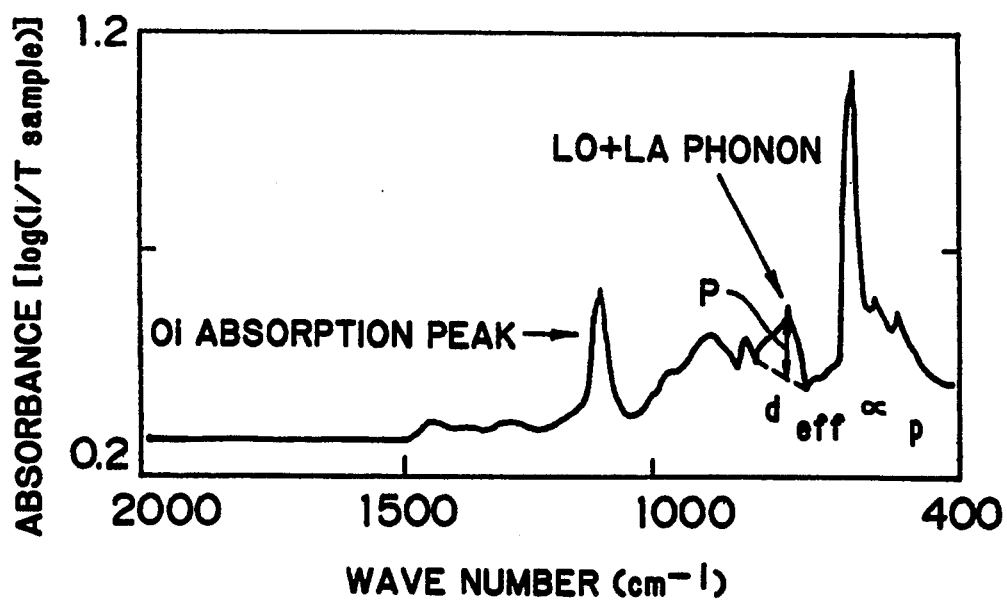
FIG. 6 is an absorbance spectrum diagram for the explanation of the effective thickness $d_{eff}$ of a sample to be used by the conventional B method.

In the [Oi] determination using the B method, the data points in FIG. 3 implies that the term $\alpha_{o,eff} \approx \ln(1/T)/d_{eff}$ in the [Oi] conversion formula 8 possesses a strong temperature dependence as seen in FIG. 3. The term $\ln(1/T)$ stands for the peak height and it has the temperature dependence eqivalent to the [Oi] values evaluated by the A method. This statement means that the strong temperature dependence of the value of evaluation of [Oi] by the B method (the temperature dependence of $\alpha_{o,eff}$) combines the temperature dependence of the peakheight [$\ln(1/T)$] with the temperature dependence of $d_{eff}$. To be more specific, the peak height p (FIG. 6) of the LO+LA phonon which fixes the term $d_{eff}$ inaccordance with the formula 6 increases in proportion as the sample temperature increases even when the actual sample thickness is the same.

Figure 7:
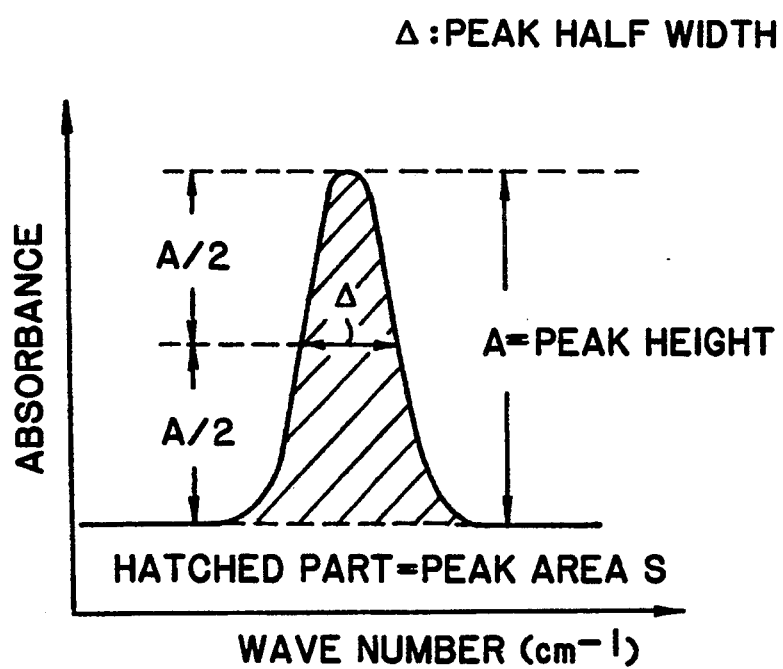
FIG. 7 is a model diagram for aiding in explaining the definitions of peak half width, peak height, and peak area of the absorption peak.

In these circumstances, highly accurate determination is not easily obtained when the A method or B method is used, especially when the B method is used. For the purpose of solving these problems on the method of determination, it is important to devise a magnitude other than $\alpha_o$ or $\alpha_{o,eff}$ which possesses a relation of proportion to [Oi] and shows only sparing dependency on the sample temperature. First, (light absorption coeffi cient)×(peak half width) was regarded as a physical quantity expressing the intensity of Oi absorption other than $\alpha_o$ and (peak area) as a similar physical quantity and these physical quantities were studied for their dependency on the sample temperature. The definitions of peak height, peak half width, and peak area are as shown by the model diagram of FIG. 7. The term $\alpha_o$ stands for the light absorption coefficient which corresponds to the peak height at 1106 cm$^{-1}$.

The conversion of [Oi] based on (light absorption coefficient)×(peak half width)

is expressed by the formula 9:

$$[Oi] = k_1 \alpha_o \Delta \quad \text{[Formula 9]}$$

wherein $\Delta$ stands for the peak half width. Then, the conversion of [Oi] based on the peak area S is expressed by the formula 10.

$$[Oi] = k_2 S \quad \text{[Formula 10]}$$

In the formula 9 and the formula 10 $k_1$ and $k_2$ each stand for the concentration conversion coefficient to be obtained in the relevant case with a Si single crystal having a standard oxygen concentration. The values of evaluation of [Oi] obtained by the formula 9 and the formula 10 were examined for their dependency on the sample temperature. The results are indicated respectively by the marks $\Delta$ and the marks + in the diagram of FIG. 3. Since (light absorption coefficient)×(peak half width) and (peak area) are substantially equal magnitudes as clearly noted from FIG. 7, the mark $\Delta$ and the marks+ in FIG. 3 show virtually equal behaviors. The following description, therefore, will treat of (light absorption coefficient)×(peak half width), namely the formula 9, exclusively.

What should be noted from FIG. 3 at this state is the fact that the dependency of the term $\alpha_o \Delta$ on the sample temperature is such that, contrary to that which exists in the determination by the A method (the determination based on $\alpha_o$), the term tends to increased though slightly in proportion as the sample temperature increases. It is easily understood, therefore, that the term in question has a relation of proportion to [Oi] and that the physical quantity having only small dependency on the sample temperature can be realized by a proper weighed mean of $\alpha_o$ and $\alpha_o \Delta$. In the following formula 11 of weighed mean, $$[Oi] = k_2(\alpha_o + a\alpha_o\Delta) = k_2\alpha_o(1+a\Delta) \quad \text{[Formula 11]}$$

the dependency on the sample temperature expressed by the formula 11 is minimized when the weight factor a of the weighed mean of $\alpha_o$ which corresponds to (peak height) and $\alpha_o \Delta$ which corresponds to (light absorption coefficient)×(peak half width) is properly selected. The concentration conversion coefficient $k_s$ is fixed by measuring a Si single crystal sample of a standard oxygen concentration. As specifically described in the working examples to be cited hereinbelow, it has been found that stable determination yielding a substantially invariable value of evaluation of [Oi] is obtained in spite of a possible change of the sample temperature when the formula 11 is applied to the suitably selected weight factor a.

Entirely the equivalent results are obtained by using the weighed mean of $\alpha_o$, corresponding to (peak height) and (peak area) S in the place of the formula 11 with respect to a proper weight factor b. In this case, the following formula 12 corresponds to the formula 11.

$$[Oi] = k_4 \alpha_o(1 + bS/\alpha_o) \quad \text{[Formula 12]}$$

wherein $k_4$ stands for a concentration conversion coefficient.

Now, the apparatus will be described which is contemplated by this invention for the determination of an interstitial oxygen concentration in a silicon single crystal.

In the apparatus for determination according to this invention, a sample stage thereof is provided with temperature adjusting means.

When the sample stage is not provided with the temperature adjusting means, the trend of the result of determination decreasing or increasing with the rise of the temperature of the sample crystal will become prominent without reference to the choice among the methods shown in FIG. 3 which are generally adopted for concentration conversion. This method, therefore, contemplates obtaining accurate results of determination by providing the sample stage with the temperature adjusting means thereby maintaining the sample stage at a constant temperature.

The method for determination according to this invention aims to obtain an accurate interstitial oxygen concentration by making use of the fact that while the general value of evaluation of [Oi] based on the peak at 1106 cm$^{-1}$ is varied as shown in FIG. 3 by the change in temperature of the sample temperature, the value of evaluation of [Oi] found by the formula 11 or the formula 12 has virtually no dependence on the sample temperature. The apparatus for determination according to this invention aims to obtain an accurate interstitial oxygen concentration by providing the sample stage with the temperature adjusting means thereby maintaining the temperature of the sample stage and consequently the temperature of the sample at a constant level and preventing the sample from change of temperature.

Further, in the apparatus for determination according to this invention, the part accommodating the light source, the interferometer, and the electric circuit is perfectly separated spatially from the sample chamber so as to preclude the possibility of the atmospheric gas of a higher temperature in the part accommodating the light source, for example, flowing into the sample chamber and consequently raising the temperature of the sample crystal. Thus, the part for accommodating the light source and other heat-generating devices and the sample chamber are separated from each other by means of a partition panel and even the path for the infrared light is partitioned with an optical window member capable of passing the infrared light. Owing to the partitioning measures mentioned above, the internal temperature of the sample chamber does not differ very much from the temperature of the measuring chamber and the temperature of the sample is changed only sparingly when the sample is introduced into the sample chamber even when the sample stage is not provided with the temperature adjusting means. The desire to obtain highly accurate determination of an interstitial oxygen concentration, therefore, is perfectly fulfilled by additionally adopting the method of evaluation of [Oi] of the formula 11 or the formula 12 which has only small dependence on the sample temperature in the conversion of Oi concentration.

The apparatus for determination of this invention is also endowed with a function of automatically determining the thickness of a sample which is necessary for the calculation of the light absorption coefficient $\alpha_o$ in the formula 11 or the formula 12. It is adapted to effect comprehensive computerized control of such operations as measurement of infrared absorption, calculation of [Oi], and automatic conveyance of the sample so as to ensure perfect automation of the accurate determination of [Oi].

Figure 2:
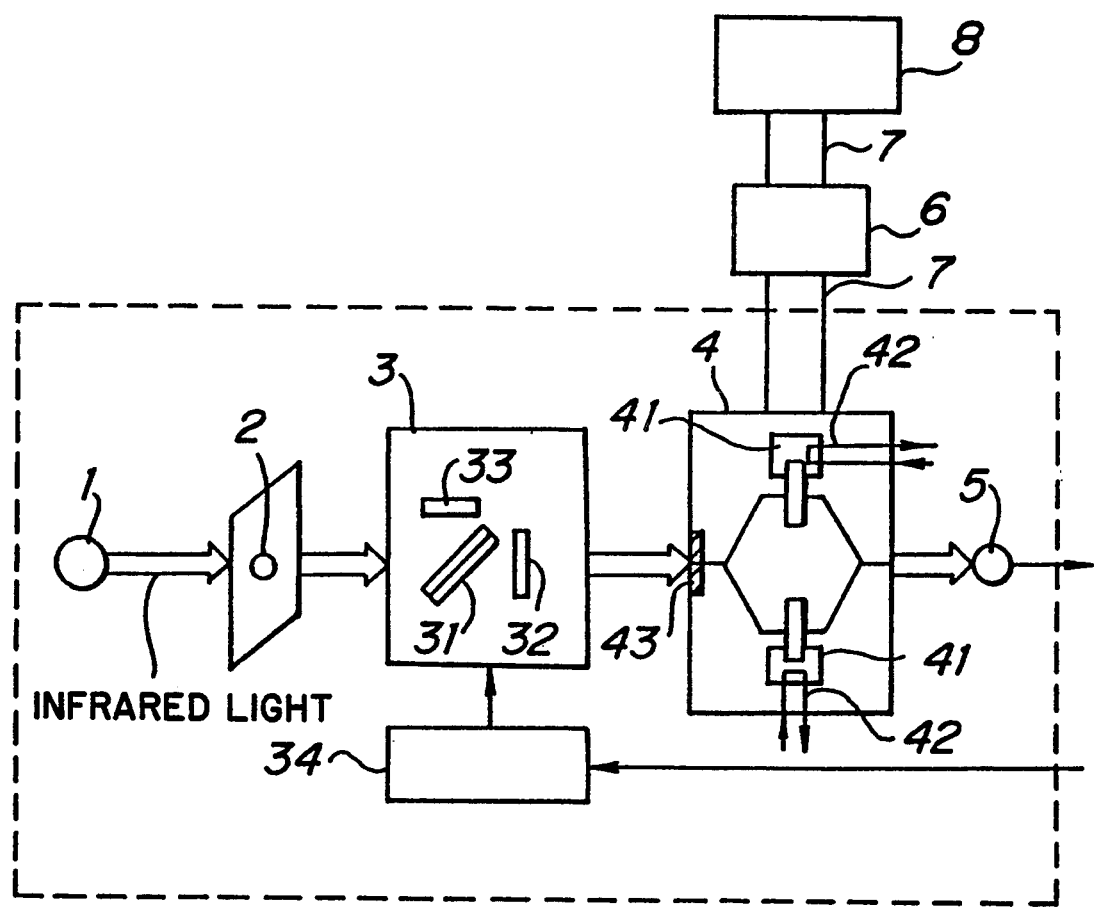
FIG. 2 is an explanatory diagram schematically illustrating the construction of the apparatus of determination according to the present invention.

FIG. 2 illustrates schematically the construction of the apparatus for determination of this invention.

In FIG. 2, 1 stands for a light source for infrared light. Generally, a Globar light source which is obtained by sintering silicon carbide (SiC) of the shape of a rod may be used as the light source. The Globar light source possesses a spectral distribution closely resembling a blackbody radiation and has a working wave number range approximately between 9000 and 100 cm$^{-1}$. Alternatively, a ceramic light source of the shape of a rod can be used as the light source herein.

In the diagram, 2 stands for an incidence orifice and 3 for an interferometer. The incidence orifice 2 serves the purpose of limiting the light from the light source 1 and, at the same time, intercepting the part of the light impinging on an interferometer 3 which is the angular greater than an angle fixed by the diameter of the orifice of the optimum incidence.

The interferometer 3 is provided with a translucent mirror 31 for dividing the incident light into two parts, a movable mirror 32 for returning the two separated parts of the light back to the translucent mirror 31, and a stationary mirror 33. The movable mirror 32 is moved parallelly to the light axis to play the role of changing the difference of light path of the interferometer 3. A movable mirror drive mechanism which is denoted by 34 is so controlled with a computer omitted from the illustration as to impart a motion to the movable mirror.

By 4 is denoted a sample chamber. In the sample chamber 4, a sample stage 41 for fixation of a sample thereto is disposed. This sample stage 41 is provided with temperature adjusting means 42. The temperature adjusting means 42 may be a pipe which is adapted to allow flow therethrough of a medium kept at a fixed temperature and buried in the sample stage 41 so as to maintain the sample stage 41 at a fixed temperature by virtue of the endothermic or exothermic action of the medium. The temperature adjusting means 42 may be otherwise a device which is adapted to produce a cooling action by virtue of the Peltier effect and is buried in the sample stage 41 so as to maintain the sample stage at a fixed temperature by adjusting the amount of electric current flowing to the device. Alternatively, it may be a heater which is endowed with a temperature adjusting function and is buried in the sample stage 41 so as to maintain the sample stage 41 at a fixed temperature. Into the sample fixed on the sample stage 41 inside the sample chamber 4, the light emitted from the interferometer 3 is projected. The light which has entered into the sample and the passed therethrough or reflected thereby after absorption of the light of a characteristic wave number peculiar to the sample under test is detected by a detector 5.

For the purpose of perfectly partitioning the sample chamber 4 from the part accommodating the light source and the interferometer, the part of the partition panel of the sample chamber for allowing passage of the infrared light is partitioned perfectly with an optical window member 43 which is capable of passing the infrared light. The partitioning structure precludes the possibility of the warmed atmospheric gas in the part accommodating the light source and the interferometer flowing into the sample chamber. The optical window member 43 may be made of cesium iodide (CsI) or potassium bromide (KBr), for example.

The sample chamber 4 is connected to a contacting or noncontacting automatic thickness measuring device 6 and a sample crystal storing part 8 through the medium of an automatic sample conveying system 7. The motions of these devices coupled with such operations as measurement of infrared absorption with a spectrophotometer and calculation of interstitial oxygen concentration and relevant data processing are collectively controlled by means of a computer so as to allow perfect automation of the determination of [0I] by the formula 11 or the formula 12 which requires measurement of the thickness of a sample.

In the first aspect of this invention, i.e. the method for determination of an interstitial oxygen concentration of a silicon single crystal, the interstitial oxygen concentration is obtained of the absorption peak at 1106 cm$^{-1}$ in accordance with the formula 11 or the formula 12. Thus, the value of an interstitial oxygen concentration being determined can be prevented from being varied by a possible change of the temperature of the sample crystal during the course of determination.

The apparatus for determination of the present invention can eliminate possible variation of the value of evaluation of [Oi] by providing the sample stage with the temperature adjusting means thereby maintaining the temperature of the sample stage and consequently the temperature of the sample at a fixed level.

Also by perfectly partitioning the sample chamber from the part accommodating the light source, the interferometer, and the electric circuit with the optical window member disposed in the opening part allowing penetration therethrough of the light path for the infrared light, the change of the temperature of the sample crystal can be curbed. In the state consequently created, the possible variation of the value of determination [Oi] can be eliminated by carrying out the calculation of [Oi] based on the formula 11 or the formula 12.

By combining the apparatus for determination described above with the function for automatic measurement of the thickness of a sample and the automatic sample conveying system, highly accurate determination of [Oi] by the formula 11 or the formula 12 can be perfectly automated by virtue of the control with a computer.

The method for determination and the apparatus for determination described above both enable the interstitial oxygen concentration in a silicon single crystal to be determined with high accuracy.

In the fifth aspect of this invention, the Oi peak which 1720 cm$^{-1}$ is held to be based on the combination of the phonon union TA+TO of the silicon lattice with the antisymmetric streching mode of vibration of $Si_2O$ according to the monograph proposed by B. Pajot et al. This peak does not overlap the absorption band of oxygen precipitate at 1300 to 1000 cm$^{-1}$ found in FIG. 10, indicating that the absorption of interstitial oxygen alone participates in the formation of this peak. By using the peak height, area, or (half width)× (peak height) of this particular peak, therefore, the interstitial oxygen concentration in a silicon single crystal having oxygen precipitate therein can be determined accurately.

Now, this invention will be described more specifically below with reference to working examples.

EXAMPLE 1

First through fourth aspects of the invention

A silicon single crystal rod was pulled by the Czochralski method. The produced single crystal rod was cut with a diamond saw. The piece cut from the single crystal rod was subjected to lapping, chemical etching, washing, and mirror polishing to obtain a silicon slab having the opposite surfaces thereof finished in mirror smoothness.

The slab of mirror surfaces was processed with a Fourier-transform infrared spectrophotometer (FT-IR) to obtain an absorption peak at 1106 cm$^{-1}$ inducive of the absorption of the interstitial oxygen in the slab in the infrared local vibration mode and investigate the relation between the sample temperature and the value of evaluation of [Oi] by the formula 11.

FIG. 1 illustrates the relation between the value of evaluation of [Oi] by the formula 11 and the sample temperature. The data reflect the fact that 0.015 was adopted as the weight factor a of the weighed mean in the formula 11. It is clearly noted from FIG. 1 that the method of this invention allows stable and accurate determination of the interstitial oxygen concentration and the result of this determination is varied only sparingly by the change in the sample temperature.

EXAMPLE 2

First through fourth aspects of the invention

Figure 8:
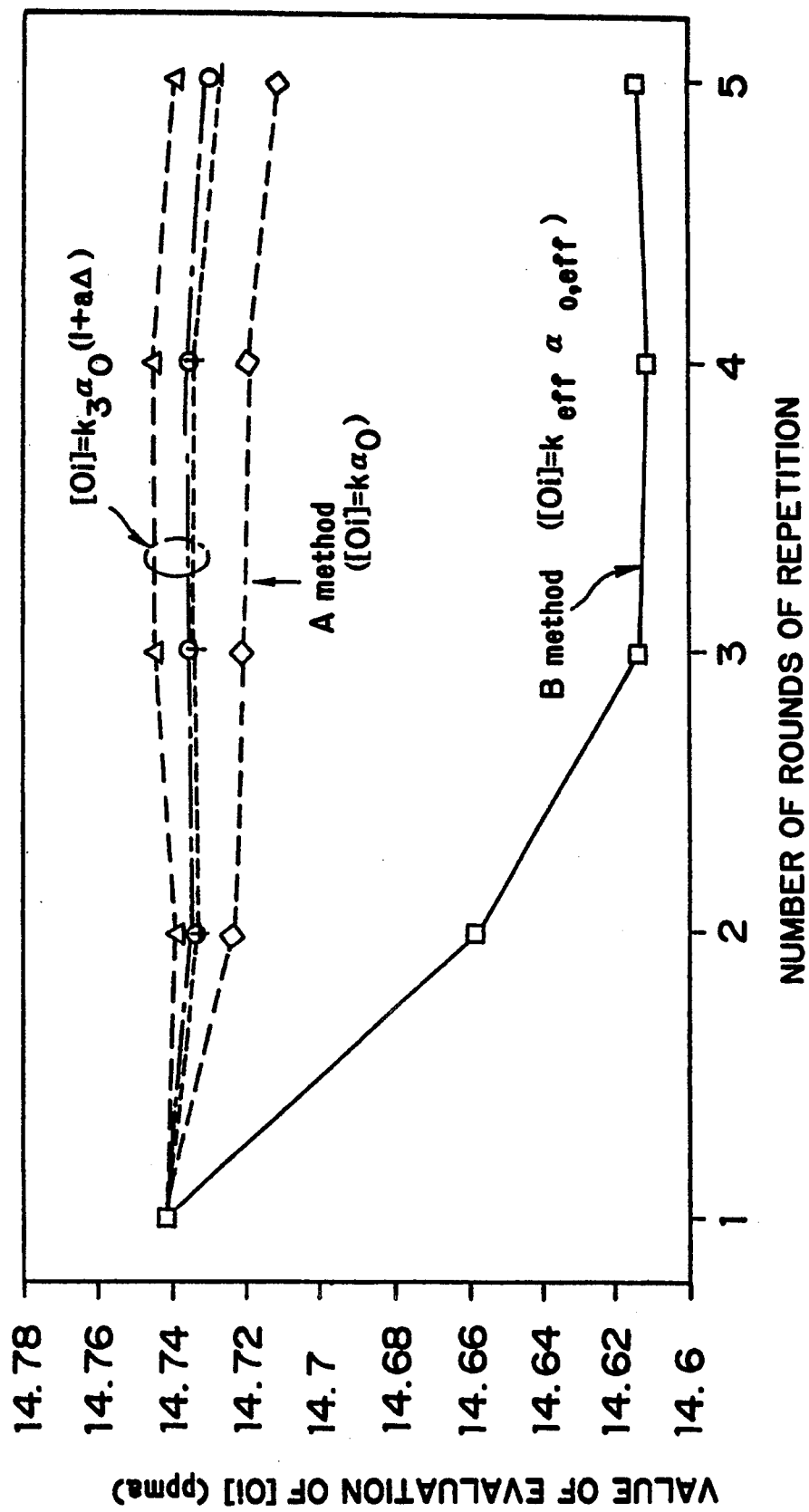
FIG. 8 is a graph showing the state of changes occurring in the repeated determination of the values of evaluation of the interstitial oxygen concentration in Examples 2, 3, and 4 and Comparative Experiment 2.

An Oi absorption peak at 1106 cm$^{-1}$ was obtained of the same sample as used in Example 1. This Oi absorption peak was subjected to repeated evaluation of [Oi] by using the formula 11 and the weight factor, a=0.015. In this case, the temperature adjustment of the sample stage and the provision of the partition of the optical window member 43 of FIG. 2 were both omitted. The results are shown by the marks Δ in FIG. 8. The data of the first determination were those obtained during the cumulative period of one minute immediately following the insertion of the sample in the sample chamber. The second determination was started immediately after completion of the first determination and continued similarly for the cumulative period of one minute. The sample was left untouched between the first and second rounds of determination. The temperature of the sample gradually rose from the first through the second round of determination. The one-minute determination was repeated in the third and following rounds. It was found by the experiment that the use of the formula 11 yielded results of ideal repeatability even when the temperature of the sample was not controlled.

EXAMPLE 3

First through fourth aspect of the invention

The repetition of evaluation of [Oi] by the formula 11 was carried out by following the procedure of Example 2. In this case, the temperature of the sample stage was adjusted to control the temperature of the sample at 28° C. The results are shown by the marks + in FIG. 8. The data indicate that the determination produced results equal to or better than those of Example 2 with high stability and repeatability.

EXAMPLE 4

First through fourth aspects of the invention

The repetition of evaluation of [Oi] by the formula 11 was carried out by following the procedure of Example 2. In this case, the adjustment of the temperature of the sample stage was omitted and the apparatus for determination was provided with a partition of an optical window member 43 of FIG. 2 to prevent inflow of a warm atmospheric gas from the part accommodating the light source and other heat-generating devices. The determination was repeated with the temperature of the sample chamber kept at 25° C., namely the normal room temperature. The results are shown by the marks ○ in FIG. 8. The data indicatate that the determination produced results equal to or better than those of Example 2 with high stability and repeatability.

COMPARATIVE EXPERIMENT 1

The relation between the value of evaluation of [Oi] in a silicon single crystal and the sample temperature of the silicon single crystal was obtained by following the procedure of Example 1, excepting the values of evaluation of [Oi] obtained of the absorption peak at 1106 cm$^{-1}$ by the A method and the B method were used as the values of determination. The results are shown respectively by the marks ◇ and the marks □ in FIG. 3.

It is clearly noted from FIG. 3 that the values of evaluation of [Oi] obtained by the A method and the B method both decreased in proportion as the sample temperature rose and an exact result of determination was difficult to obtain. The determination using the B method particularly showed conspicuous dependency on the sample concentration and the method encountered a great difficulty in effecting highly accurate determination.

COMPARATIVE EXPERIMENT 2

The determination for evaluation of [Oi] was repeated by following the procedure of Example 2, excepting the values of evaluation of [Oi] obtained of the absorption peak at 1106 cm$^{-1}$ by the A method and the B method were used as the values of determination. The results are shown respectively by the marks ◇ (the A method) and the marks □ (the B method) in FIG. 8. In both the cases, the values of evaluation of [Oi] decreased in proportion as the number of rounds of determination increased and the sample was warmed by the atmospheric gas in the sample chamber. Particularly in the determination by the B method, the values of evaluation in the first three rounds of determination largely varied to render accurate determination difficult.

EXAMPLE 5

Fifth aspect of the invention

A silicon single crystal rod was pulled by the Czochralski method. The produced single crystal rod was cut with a diamond saw. The piece of the single crystal rod was subjected to such treatments as lapping, chemical etching, washing, and mirror polishing to obtain a silicon slab 2 mm in thickness having the opposite surfaces finished in mirror smoothness.

The silicon slab having surfaces of mirror finish was set in place in a sample chamber of a FT-IR apparatus. The interior of the apparatus and the interior of the sample chamber were purged with nitrogen gas whose pressure dew point of moisture was not higher than $-73°$ C. The FT-IR determination was started after the absorption peak due to the moisture near 1720 cm$^-$ was confirmed to have fallen below the lower limit of detection.

As the reference crystal to be used for obtaining a difference spectrum of Oi absorption, a Si single crystal of the floating zone method (FZ method) containing Oi in a concentration below the lower limit of detection, exhibiting resistivity of 100 Ω cm, measuring 2 mm in thickness, and having the opposite surfaces finished in mirror smoothness was used. The interstitial oxygen concentration in the silicon single crystal was obtained from the magnitude of peak height of the absorption peak at 1720 cm$^{-1}$ in the difference spectrum mentioned above. The conversion of concentration was carried out with a concentration calibration curve of the peak at 1720 cm$^{-1}$ obtained of a separately prepared Si single crystal sample having a standard oxygen concentration.

Figure 12:
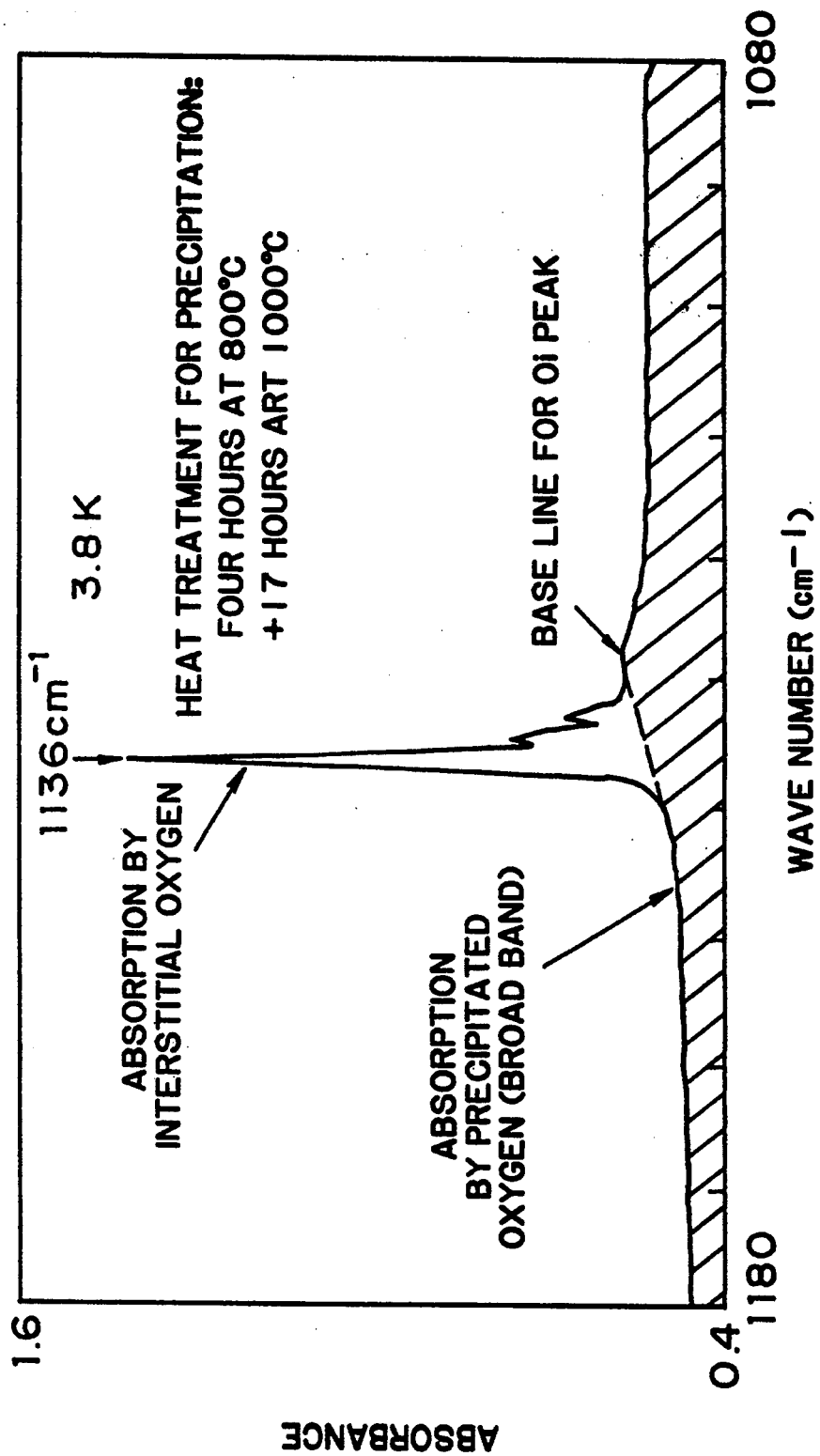
FIG. 12 is a graph showing the infrared absorption spectrum obtained of an oxygen-precipitated silicon single crystal at the low temperature of 3.8 K. and the separation of the Oi absorption peak and the oxygen precipitate absorption band.

Separately, the reliable value of [Oi] was obtained by the method for separating the oxygen precipitate absorption band and the interstitial oxygen absorption peak by means of the FT-IR spectrophotometer at the low temperature of 3.8 K. The infrared absorption spectrum obtained by this method is shown in FIG. 12.

Figure 9:
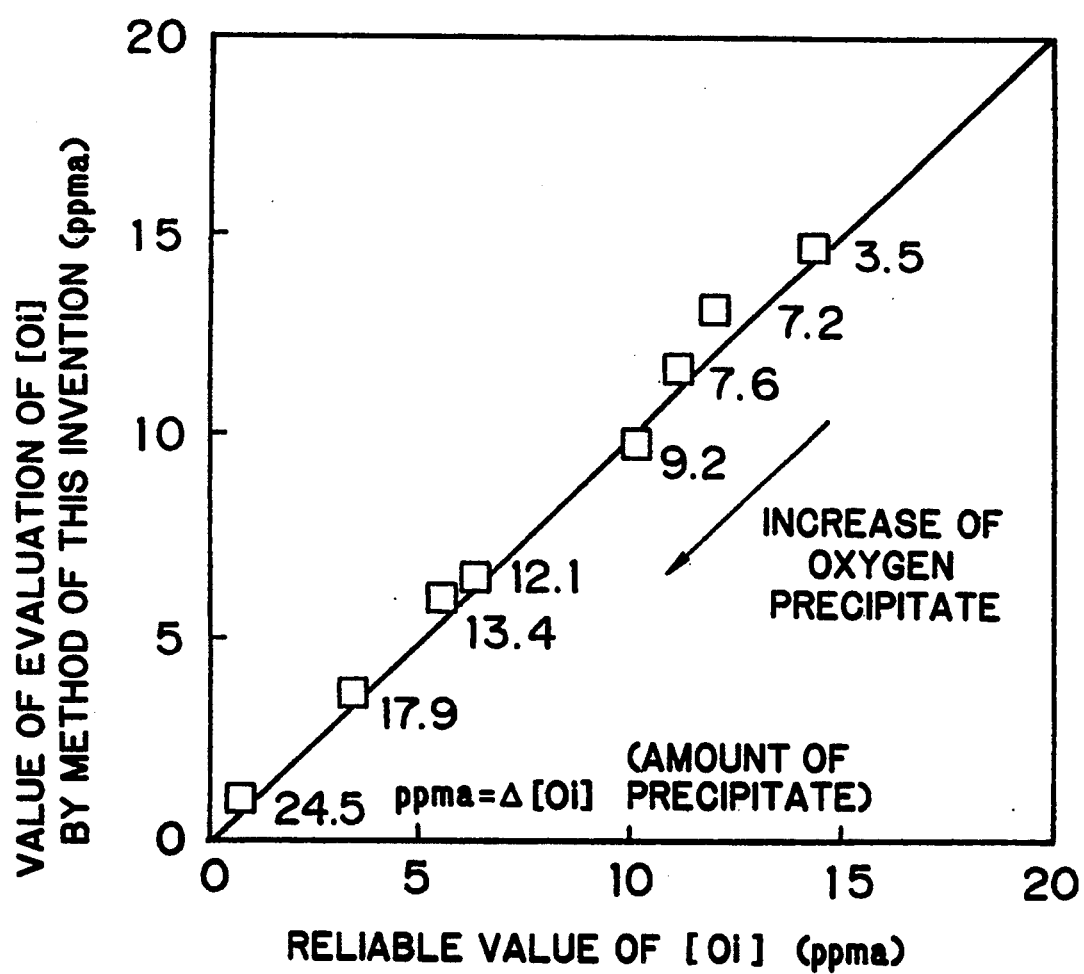
FIG. 9 is a graph showing the relation between the value of evaluation of the interstitial oxygen concentration obtained by the method of the fifth aspect of this invention and the reliable value of [Oi] obtained by the method of determination at the low temperature of 3.8 K.

Then, the value of evaluation of [Oi] obtained from the peak height of the absorption peak appearing at 1720 cm$^{-1}$ at the normal room temperature was compared with the reliable value of [Oi] obtained by the Oi peak absorption at 3.8 K. The results are shown in FIG. 9. It is clearly noted from this diagram that by the use of the present method which obtains the interstitial oxygen concentration in a silicon single crystal from the peak height of the absorption peak appearing at 1720 cm$^{-1}$ at normal room temperature, an accurate value of evaluation of [Oi] can be easily obtained even in an oxygen-precipitated crystal.

The determination by the use of the area or that by the use of (half width)×(peak height) of the peak at 1720 cm$^{-1}$ were also investigated. The results were similar to those obtained by the use of the peak height.

COMPARATIVE EXPERIMENTS 3 AND 4

The same silicon slabs having surfaces finished in mirror smoothness as used in Example 5 were processed with the FT-IR spectrophotometer to obtain infrared absorption spectra. The results are shown in FIG. 10.

In the infrared spectra, a base line was drawn between 1300 cm$^{-1}$ and 900 cm$^{-1}$. From the peak height above the base line, the value of evaluation of [Oi] was obtained (the A method for Comparative Experiment 3) in accordance with the method of concentration conversion standardized by Japan Electronic Industry Development Association (JEIDA) [T. Iizuka et al., J. Electrochem. Soc., 132, 1707 (1985)].

The values of evaluation of [Oi] was plotted in comparison with the reliable value of [Oi] obtained by the separation of the Oi peak at 3.8 K. The results are shown by the marks ○ in FIG. 11.

In the aforementioned infrared absorption spectrum, a base line was drawn between 1150 cm$^{-1}$ and 1050 cm$^{-1}$. From the peak height above this base line, the value of evaluation of interstitial oxygen concentration [Oi] was obtained in the same manner as described above (the B method for Comparative Experiment 4).

The value of evaluation of [Oi] was plotted in comparison with the reliable value of [Oi] obtained by the separation of the Oi peak at 3.8 K. The results are shown by the marks △ in FIG. 11.

Figure 11:
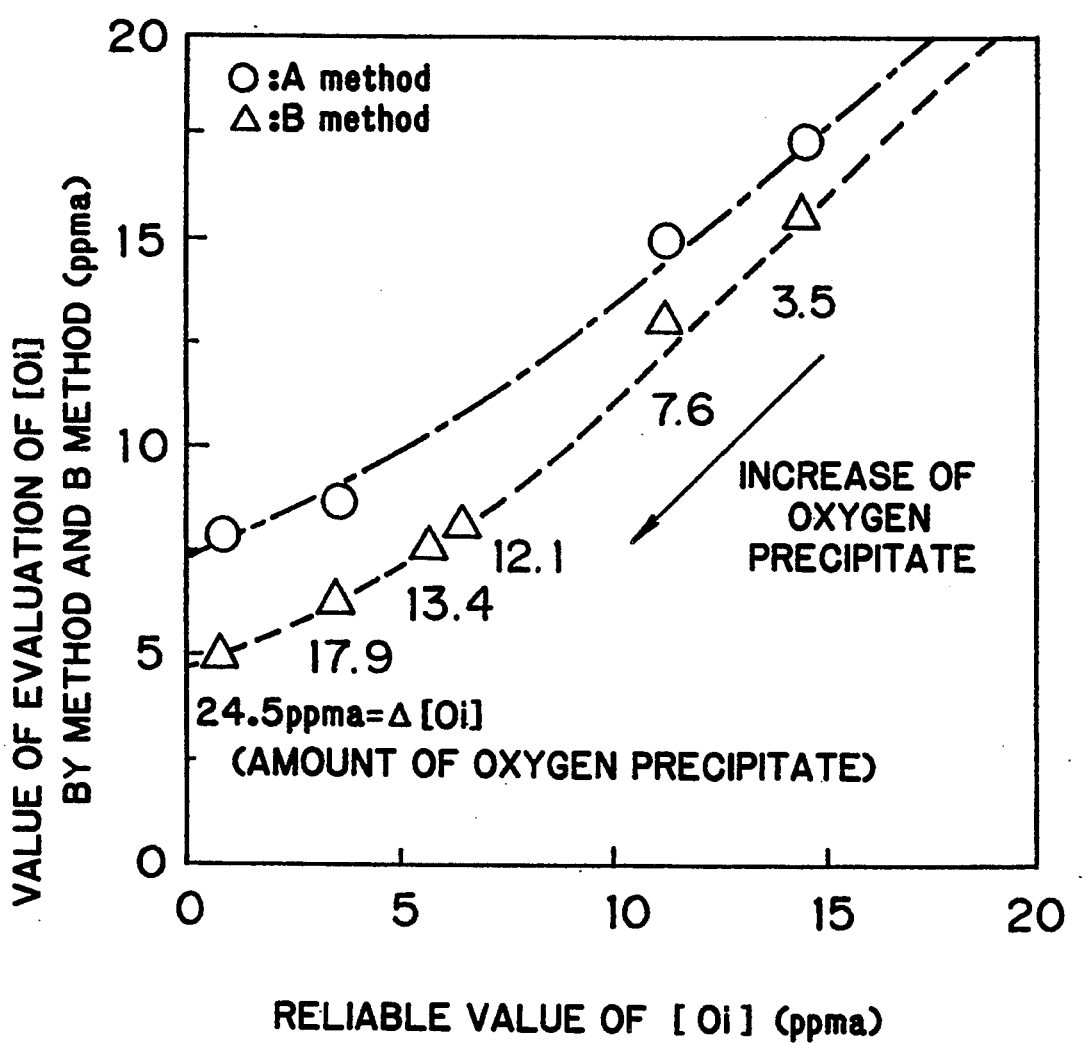
FIG. 11 is a graph showing the relation between the values of evaluation of the interstitial oxygen concentration [Oi] obtained by the A method and the B method and the reliable value of [Oi] obtained by the determination at the low temperature of 3.8 K.

It is clearly noted from FIG. 11 that the values obtained in Comparative Experiment 3 (A method) and Comparative Experiment 4 (B method) largely deviated from the reliable value of [Oi]. This is because the absorption peak based on the interstitial oxygen at 1106 cm$^{-1}$ overlapped the absorption peak based on the oxygen precipitate and the two methods mentioned above each obtained the value of evaluation of [Oi] without separating the overlapping peaks in advance.

It is clear from the description given thus far that the method for determination of the interstitial oxygen concentration in a silicon single crystal according to this invention (the first aspect of this invention), the determination of the interstitial oxygen concentration can be stably and accurately carried out without being appreciably affected by the sample temperature.

The apparatus for determination of the interstitial oxygen concentration in a silicon single crystal according to this invention (the second aspect of this invention) allows the determination to be carried out with the temperature of the sample stage and consequently the temperature of the sample itself within the apparatus kept at a constant level and, therefore, enables the interstitial oxygen concentration in the silicon single crystal to be determined stably and accurately without being affected by the change of temperature of the sample.

Further, in the apparatus for determination of the interstitial oxygen concentration in a silicon single crystal according to this invention (the third aspect of this invention), the internal temperature of the sample chamber can be substantially equalized to the temperature of the measuring chamber because the atmospheric gas in the sample chamber is perfectly separated from the atmospheric gas of a higher temperature in the part accommodating the light source and other heat-generating devices by means of the optical window member. Since virtually no change occurs in the sample temperature during the course of determination, the determination of the interstitial oxygen concentration in the silicon single crystal can be carried out stably and accurately.

By the apparatus for determination of the interstitial oxygen concentration in a silicon single crystal according to this invention (the fourth aspect of this invention), the measurement of the thickness of a sample required for working the method of this invention is effected with a contacting or noncontacting automatic thickness measuring device and such operations as measurement of infrared absorption, automatic conveyance of the sample, and calculation of the concentration of [Oi] by the method of this invention are collectively controlled with a computer to permit perfect automation of the determination.

By the fifth aspect of this invention, the interstitial oxygen concentration in a silicon single crystal having oxygen precipitate can be determined accurately by a simple procedure at normal room temperature without being obstructed by the oxygen precipitate.

What is claimed is:

1. A method for the determination of an interstitial oxygen concentration in a silicon single crystal by means of the absorption in the infrared local vibration mode of the interstitial oxygen in said silicon single crystal, which method is characterized by obtaining the absorption peak of said interstitial oxygen at $1106\ cm^{-1}$, calculating the value of:

(Light absorption coefficient)$\times [1+ax$ (half width of peak)]

or the value of:

(Light absorption coefficient)$\times [1+bx$ (peak area)/(peak height)]

(wherein a or b stands for a parameter whose value depends on the conditions of determination or the apparatus for determination and should be empirically fixed with respect to specific conditions of determination or the apparatus used therefor) concerning the absorption peak, and determining said interstitial oxygen concentration in said silicon single crystal on the basis of said value.

2. An infrared spectrophotometer as an apparatus for the determination of an interstitial oxygen concentration in a silicon single crystal, comprising a light source for the infrared radiation, an incidence orifice for limiting the light from said light source and, at the same time, intercepting the part of the light impinging on an interferometer which is the angular range greater than an angle fixed by the diameter of the orifice of the optimum incidence, an interferometer provided with a translucent mirror, a stationary mirror, and a movable mirror, a sample chamber provided with a sample stage for fixation of a sample thereto and adapted to receive the light emitted from said interferometer, and a detector for detecting the light having entered in a sample and subsequently passed therethrough or reflected thereby after absorption of the part of light of the characteristic wave number peculiar to said sample, which apparatus is characterized by the fact that the space accommodating said light source and interferometer and the space enclosing said sample chamber are partitioned from each other with the partition panel and other members of said sample chamber and the part for passing the infrared radiation is also partitioned perfectly with an optical window member and the determination of said interstitial oxygen concentration is effected by the method recited in claim 1.

3. An apparatus for the determination of an interstitial oxygen concentration in a silicon single crystal, which apparatus comprises a mechanism for inserting a sample under test into and removing said sample from a sample chamber by means of an automatic conveying device and a contacting or noncontacting mechanism for effecting automatic measurement of the thickness of said sample before or after the measurement of infrared absorption, performs comprehensive computerized control of the operations of determination of infrared absorption, measurement of sample thickness, computation of interstitial oxygen concentration, and conveyance of sample, and effects the determination of interstitial oxygen concentration by the method set forth in claim 1.

4. An infrared spectrophotometer in accordance with claim 3 wherein said sample stage is provided with temperature adjusting means.

5. A method for the determination of an interstitial oxygen concentration of a silicon single crystal by the technique of infrared absorption, which method is characterized by effecting said determination of the interstitial oxygen concentration in said silicon single crystal on the basis of the height or area of the absorption peak appearing at $1720\ cm^{-1}$ or the value of (half width)$\times$(peak height) and wherein said determination is carried out under an atmosphere of a purge gas having no infrared absorption near $1720\ cm^{-1}$.

* * * * *